(12) United States Patent
Tanaka et al.

(10) Patent No.: US 7,384,427 B2
(45) Date of Patent: Jun. 10, 2008

(54) STENT

(75) Inventors: Yuji Tanaka, Osaka (JP); Shu Kurashima, Osaka (JP)

(73) Assignee: Nipro Corporation, Osaka-fu (JP)

( * ) Notice: Subject to any disclaimer, the term of this patent is extended or adjusted under 35 U.S.C. 154(b) by 726 days.

(21) Appl. No.: 10/487,983

(22) PCT Filed: Aug. 20, 2002

(86) PCT No.: PCT/JP02/08356

§ 371 (c)(1),
(2), (4) Date: Apr. 7, 2004

(87) PCT Pub. No.: WO03/018101

PCT Pub. Date: Mar. 6, 2003

(65) Prior Publication Data
US 2004/0254626 A1    Dec. 16, 2004

(30) Foreign Application Priority Data
Aug. 27, 2001   (JP) ............................. 2001-256012

(51) Int. Cl.
*A61F 2/00*   (2006.01)
(52) U.S. Cl. .................................... 623/1.15
(58) Field of Classification Search .............. 623/1.15, 623/1.16, 1.18; 606/192, 194, 195, 198
See application file for complete search history.

(56) References Cited

U.S. PATENT DOCUMENTS 5,707,386 A    1/1998   Schnepp-Pesch et al.
5,843,120 A *  12/1998  Israel et al. ................. 623/1.15
6,153,252 A    11/2000  Hossain et al.
6,193,747 B1 * 2/2001   von Oepen ................. 623/1.15

FOREIGN PATENT DOCUMENTS

| EP | 0688545 A1 | 12/1995 |
| EP | 1042997 A1 | 10/2000 |
| WO | WO 99/01088 A1 | 1/1999 |

* cited by examiner

Primary Examiner—Kevin T. Truong
(74) Attorney, Agent, or Firm—Birch, Stewart, Kolasch & Birch, LLP

(57) ABSTRACT

A stent is a tubular member comprising cylindrical lumen size-holding portions 1 for holding a lumen of a living body open, and connecting portions 2 for longitudinally connecting the lumen size-holding portions 1 adjacent to one another. The lumen size-holding portions 1 are configured into repeated patterns running vertically in the developed conditions thereof. Each of the repeated patterns comprises a first curved pattern portion 11 having axis extending in a lateral direction and second and third curved pattern portions 12 and 13 having axes extending in vertical directions. The upper and lower first curved pattern portions 11 adjacent to one another are connected at one end thereof by the second curved pattern portion 12, and at the other end by the third curved pattern portion 13. The stent is excellent in flexibility and trackability to lumens. Further, the stent is capable of being passed through three-dimensionally meandering lumens and possesses a sufficient strength for holding a widened size of a lumen.

20 Claims, 8 Drawing Sheets

STENT

TECHNICAL FIELD

The present invention relates to stents to be implanted in a living body to maintain a size of a lumen such as blood vessels in the living body.

BACKGROUND ART

Up to now, stents have been used to widen a lumen such as a blood vessel and then to maintain the resultant size of the lumen. Expansion of the stent may be done by various methods such as, for example, a balloon expansion process, a self-expansion process utilizing a shape memory material, a mechanical expansion process and the like. Among them, it is general practice to use a balloon expansion process. In the balloon expansion process, the stent is introduced into a desired site of a lumen in the living body along with a balloon catheter, and then expanded by inflating the balloon, thereby widening a size of the lumen. Next, the balloon is deflated and removed from the site, leaving the expanded stent in place.

The stent generally comprises lumen size-holding portions for widening and holding a size of the lumen of a blood vessel, and connecting portions for connecting these lumen size-holding portions in a longitudinal direction thereof. The stent maintains its shape after being expanded.

Various types of stents have been suggested in Japanese Patent Gazette. For example, JP-A H06-181993 discloses a stent comprising a plurality of cylinder components independently expandable in a radius direction, which are arranged around a common axis and connected to one another. JP-A S62-231657 discloses a stent comprising a tubular-shaped member expandable in a radius direction thereof and being formed by a plurality of intersecting elongated members. JP-A H08-155035 discloses a stent comprising at least two circular members each comprising a signal wire bent to form segments that are substantially straight and un-overlapped and are integrally connected at turns of the wire. JP-A H10-503676 discloses a stent comprising a tube having a patterned shape which has first and second meander patterns having axes extending in first and second directions. JP-A H11-505441 discloses a stent of open structure comprised of end-connected struts making up the parts with angular interconnects between the parts.

The aforementioned stents of the prior art have been improved in flexibility to some extent, but it is rather difficult to say that they have a sufficient flexibility. Since these stents become a burden to the inner wall of the blood vessel adjacent to edge portions of the stent, there is a fear of causing obstruction or constriction in the lumen. Further, if the lumen is of a three-dimensionally meandering structure, it is occasionally difficult to advance the stent to the desired site within the lumen. In addition, there is a fear of injuring the blood vessel during advancement of the stent to the desired site.

DISCLOSURE OF INVENTION

The present invention has been made to overcome the above problems and an object of the present invention is to provide a stent, which is excellent in flexibility and trackability to lumina, has a sufficient strength for holding a widened size of a lumen, and is capable of being passed through three-dimensionally meandering lumens.

As a result of studious efforts to solve the above problems, the inventors have achieved the present invention on the basis of the findings that the flexibility of a stent per se can be improved by providing cylindrical lumen size-holding portions with repeated patterns running vertically in the developed conditions thereof, the repeated patterns being formed by connecting a plurality of first curved pattern portions having axes extending in the lateral direction with second and third curved pattern portions having axes extending in the vertical direction. The repeated patterns make the lumen size-holding portions sufficiently extensible in both longitudinal and radial directions, while keeping a cylindrical shape thereof.

According to the present invention, there is provided a stent improved in flexibility and comprised of a tubular member comprising cylindrical lumen size-holding portions for holding a lumen of a living body open, and connecting portions for longitudinally connecting said lumen size-holding portions adjacent to one another, wherein said lumen size-holding portions are configured into repeated patterns running vertically in the developed conditions thereof, said repeated pattern comprising: first curved pattern portions arranged in parallel with one another and each having first and second ends and an axis extending in a lateral direction; second curved pattern portions having axes extending in a vertical direction and each connecting the first end of said first curved pattern portion located at an even-numbered position from the bottom and the first end of the first curved pattern portion located on the downside of said even-numbered, first curved pattern portion; and third curved pattern portions having axes extending in the vertical direction and each connecting the second end of the first curved pattern portion located at the even-numbered position and the second end of the first curved pattern portion located on the upside of said even-numbered, first curved pattern portion.

In the present invention, the term "curved patterns" include kneed or angled patterns. Thus, the curved patterns include patterns such as, for example, V-shaped, W-shaped and rectangular pulse-shaped patterns, in addition to rounded curved patterns such as arc-shaped, oval-shaped and sine wave-shaped patterns.

In a preferred embodiment, the first curved pattern portion is composed of a semicircular curved portion and two straight portions extending from both ends of the curved portion. In another preferred embodiment, the first curved pattern portion is composed of a curved portion of a sine wave-shape and two straight portions extending from both ends of the curved portion.

Preferably, the longitudinally arranged neighboring lumen-size-holding portions are connected between the first end of one lumen-size-holding portion and the second end of the other lumen-size-holding portion adjacent thereto with the connecting portions. In that case, the connecting portions may be formed into a straight shape or a curved shape. It is preferred that the neighboring lumen-size-holding portions are formed in mirror symmetry in respect to the connecting portions. Further, it is preferred that the lumen size-holding portions of at least both ends of the stent are connected between every one or two repeated patterns with the connecting portions.

There is no limit for a material used for the stent, provided that the stent has a surface covered with a biocompatible material and is capable of maintaining an expanded shape thereof. It is, however, preferred to use a biocompatible material or bioabsorbable material as a material for the stent. As a biocompatible material, it is preferred to use the one selected from the group consisting of stainless steels, tungsten, tantalum and nickel-titanium alloys. Nickel-titanium alloys are used because of their shape memory effects. As a bioabsorbable material, it is preferred to use the one selected from the group consisting of polylactic acid, polyglycolic acid, polyglactin, poly(dioxanone), poly(dioxanone), polyglyconate, copolymers of polyglycolic acid and ε-caprolactam, and copolymers of lactic acid and ε-caprolactam.

The stent may be the one made of a non-biocompatible material and coated with a biocompatible material to form a biocompatible coating on a surface thereof. In that case, as a biocompatible material for the coating, there may be used those such as carbon, gold, platinum, phosphorylcholine, heparin and fibrin.

Further, the stent may be coated with a medicine for prevention of restenosis. For this end, it is preferred to use a medicine selected from the group consisting of sirolimus, taxol and actinomycin-D.

According to the present invention, it is possible to obtain the following effects. That is, the lumen size-holding portions have a sufficient strength for holding a lumen of a living body open since the lumen size-holding portions are configured into repeated patterns running vertically in the developed conditions thereof, each of the repeated patterns comprising first curved pattern portions having axes extending in a lateral direction and being arranged in parallel with one another; and second and third curved pattern portions having axes extending in the vertical direction for connecting said first curved pattern portions to one another at both ends of the same side thereof. Further, the stent is excellent in trackability to the lumen because of improvement in flexibility of the stent, and thus making it possible to reduce the load applied to the walls of the lumens as well as to allow the stent to be passed through three-dimensionally meandering lumen.

Embodiments of the present invention will be explained below with reference to the accompanying drawings, which are given by way of illustration only, and thus are not limitative of the present invention.

BEST MODE FOR CARRYING OUT THE INVENTION

Figure 1:
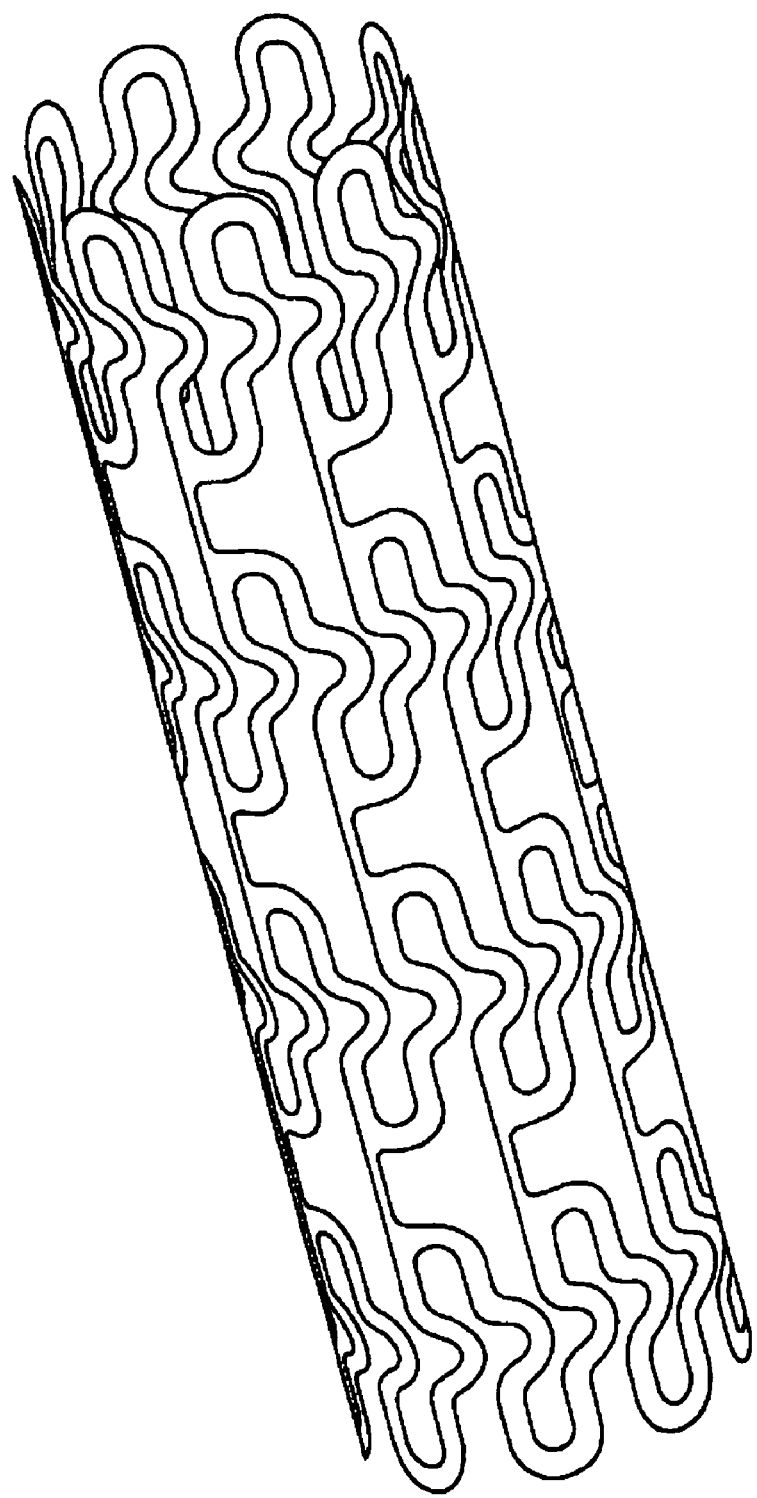
FIG. 1 is a perspective view of one embodiment of a stent according to the present invention.
Figure 2:
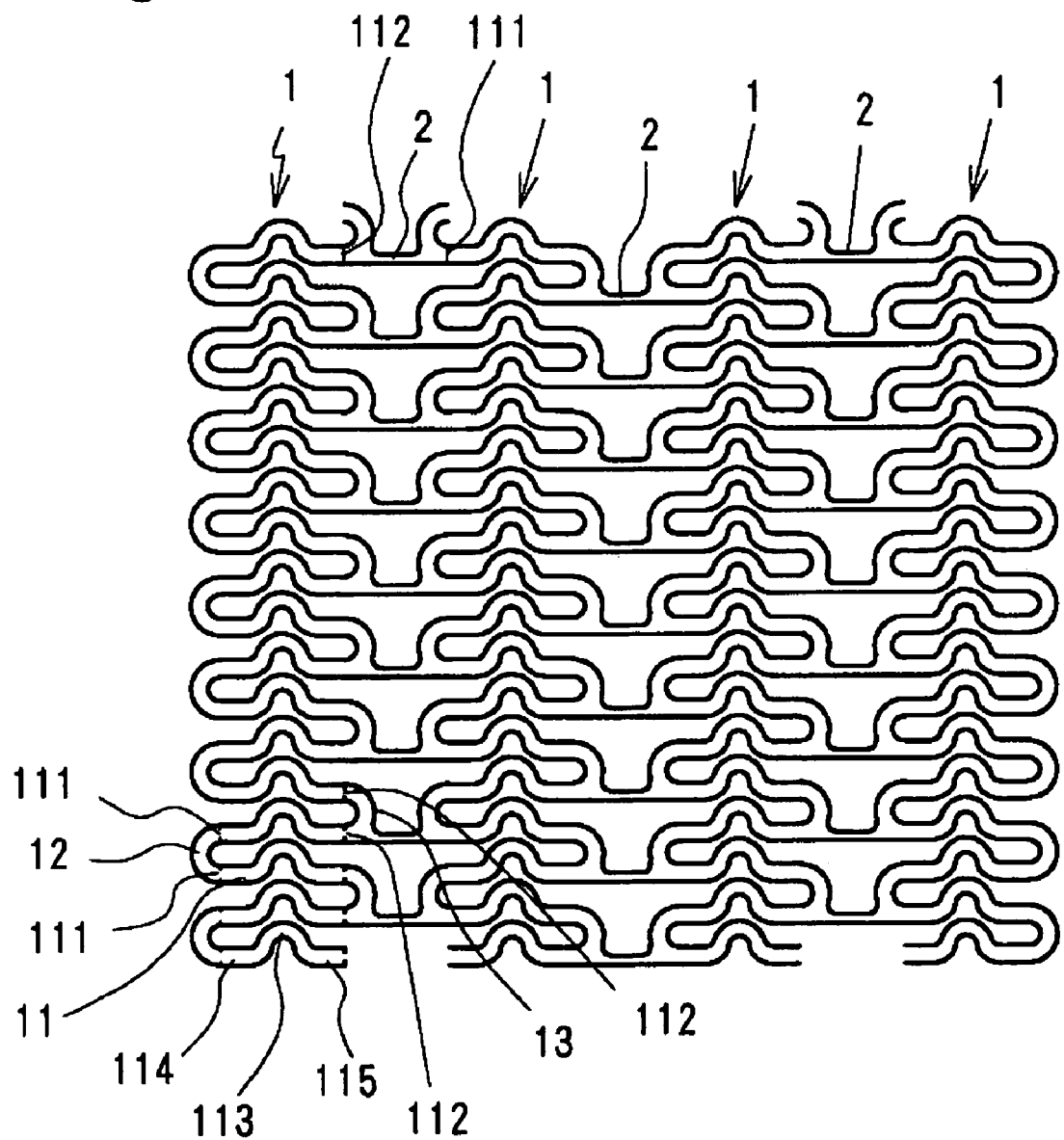
FIG. 2 is a development elevation of the stent shown in FIG. 1.
Figure 3:
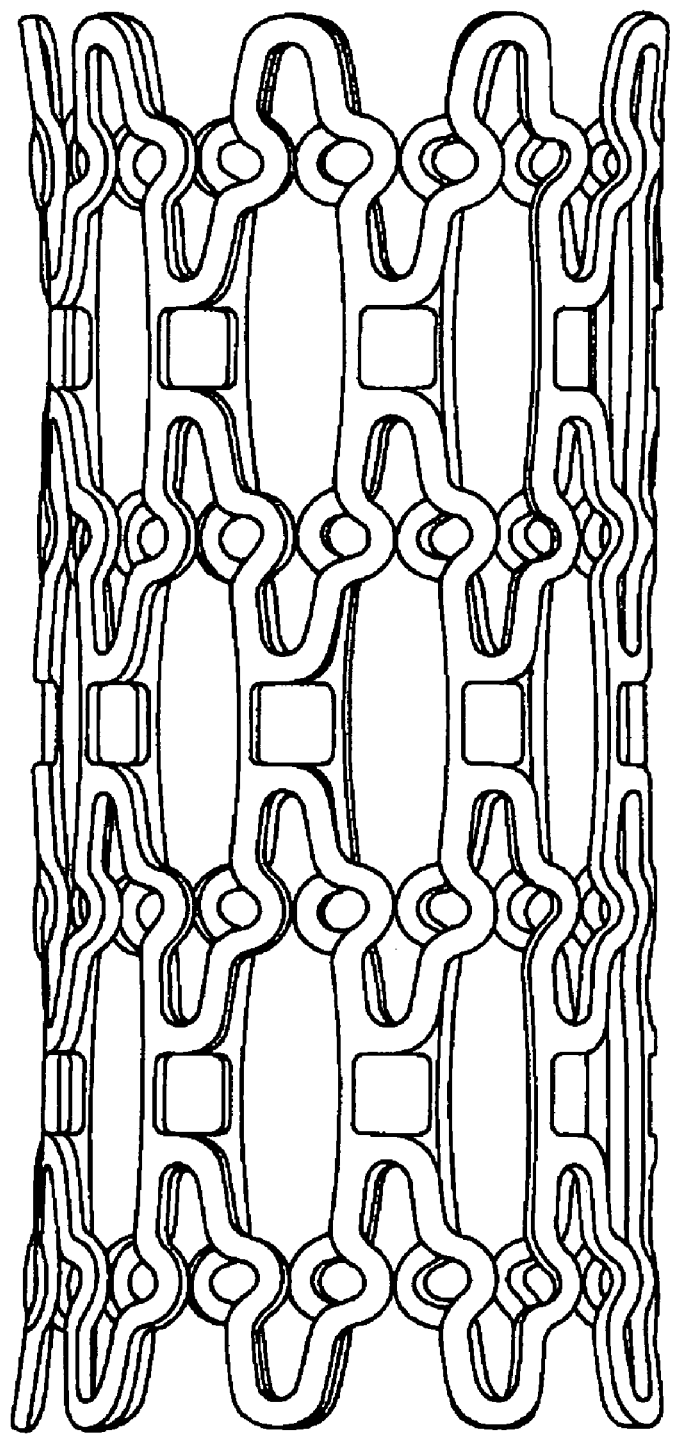
FIG. 3 is a plan view illustrating an expanded state of the stent shown in FIG. 1.

As illustrated in FIGS. 1 to 3, a stent of the present invention comprises a tubular member comprising cylindrical lumen size-holding portions 1 for holding a lumen of a living body open, and connecting portions 2 for longitudinally connecting said lumen size-holding portions 1 adjacent to one another. The lumen size-holding portions 1 are configured into repeated patterns running vertically in the developed conditions thereof. Each repeated pattern comprises a first curved pattern portion 11 having axes extending in lateral directions, and second and third curved pattern portions 12 and 13 having axes extending in upper and lower directions. The upper and lower first curved pattern portions 11 adjacent to one another are connected at one end thereof by the second curved pattern portion 12, and at the other end by the third curved pattern portion 13.

The lumen size-holding portions 1 are cylindrical components for holding the lumen of the living body open, which are configured into repeated patterns running vertically in the developed conditions thereof. The repeated patterns are comprised of first, second and third curved pattern portions 11, 12, 13. Each of the first curved pattern portions 11 comprises a semicircular curved portion 113 with a first end 111 and a second end 112, having an axis extending in a lateral direction, and two straight portions 114, 115 extending from both ends of the semicircular curved portion 113. The first curved pattern portions 11 are arranged in parallel vertically, or, in the upper and lower directions. The second curved pattern portions 12 are of a semicircular shape with an axis extending in the vertical direction. Each second curved pattern portion 12 connects the first end 111 of the first curved pattern portion 11 located at the even-numbered position from the bottom and the first end 111 of the first curved pattern portion 11 located beneath the even-numbered first curved pattern portion 11. The third curved pattern portions 13 are of a semicircular shape with an axis extending in a vertical direction, as is the case with the second curved pattern portion 12. Each third curved pattern portion 13 connects the second end 112 of the first curved pattern portion 11 located at the even-numbered position and the second end 112 of the first curved pattern portion 11 located at an upside of the even-numbered, first curved pattern portion 11.

The second and third curved pattern portions 12 and 13 have the extension axis extending in a vertical direction and thus allow the cylindrical lumen size-holding portions 1 to be expanded in the radial direction thereof. If the lumen size-holding portions 1 expand in the radial direction thereof, the longitudinal length of the lumen size-holding portions are shortened. On the other hand, the first curved pattern portions 11 have the extension axis extending in the lateral direction (left and right directions) and thus allow the cylindrical lumen size-holding portions 1 to be extended in the longitudinal direction thereof. Thus, the shortening of the stent resulting from the longitudinal shortening of the lumen size-holding portions 1 is compensated by the extension of the first curved pattern portions 11.

The connecting portions 2 are the ones for longitudinally connecting the adjacent lumen size-holding portions 1 to one another. In case that the connecting portions 2 have the same shape in cross-section, the stent is improved in flexibility and thus on in trackability by decreasing the cross sectional area, by increasing a length of the connecting portion 2 between the neighboring lumen-size-holding portions 1, and also by decreasing the number of the connecting portions 2. However, if the number of the connecting portions 2 becomes too small, parts of the lumen size-holding portions 1, which are unconnected one another by the connecting portions 2, may protrude outwardly at the time of expansion and bending of the stent. The protruded portions may cause loads acting on the wall of the lumen. In contrast therewith, the stent under the expanded or bent conditions is stabilized in cylindrical shape by increasing the number of the connecting portions 2, and the surface of the stent is smoothed. For example, if all the neighboring lumen-size-holding portions 1 are connected to one another as illustrated in FIG. 1, the stent provides a smooth surface as illustrated in FIG. 3 even in the expanded condition. However, the greater the number of connecting portions 2, the decrease is the flexibility of the stent, resulting in lowering of the trackability to the lumens, which in turn may cause considerable increase in load applied to the wall of the lumens. Accordingly, it is preferred to connect the neighboring lumen-size-holding portions 1 every one or two repeated patterns with the connecting portions 2 (cf. FIGS. 4 and 5). Further, the connection between the lumen size-holding portions 1 at both ends of the stent and the lumen size-holding portions 1 adjacent thereto may be made every one or two repeated patterns with the connecting portions 2, while connecting all the repeated patterns of the adjacent lumen size-holding portions 1 in the middle portion of the stent to one another with the connecting portions 2.

The connection of the neighboring lumen-size-holding portions 1 by the connecting portion 2 may be performed, for example, between the second curved pattern portion 12 and third curved pattern portion 13 adjacent thereto. When connection is carried out with longitudinal connecting portions 2, it is preferred to connect the one end or first end 111 of the first curved pattern portion 11 with the other end or second end 112 of the curved pattern portion 11 adjacent thereto. This makes it possible to lengthen the connecting portions 2. The connecting portion 2 may have a straight shape or a curved shape. Connection between the second curved pattern portion 12 and third curved pattern portion 13, or between the first end 111 and second end 112 may be made by a longitudinally extending connecting portions or by slantwise extending connecting portions. In light of making the connecting portion 2 longer, the connecting portions 2 are preferably made to have a shape with a curved pattern. Also, it is preferred to use slantwise connection, though it causes decrease in shape-stability of the stent.

In view of the shape stability of the stent, it is preferred that the neighboring lumen-size-holding portions 1 have mirror symmetry to the connecting portions 2. However, it is unfavorable for the shape stability to connect the lumen size-holding portions 1 with the canted connecting portions 2.

The properties of the stent such as, for example, radial stiffness, may be changed by modification of the shapes of the first, second and third curved pattern portions 11, 12, 13. Further, the number and radius of the lumen size-holding portions 1 are determined depending on a length and size of the site to be treated.

Figure 4:
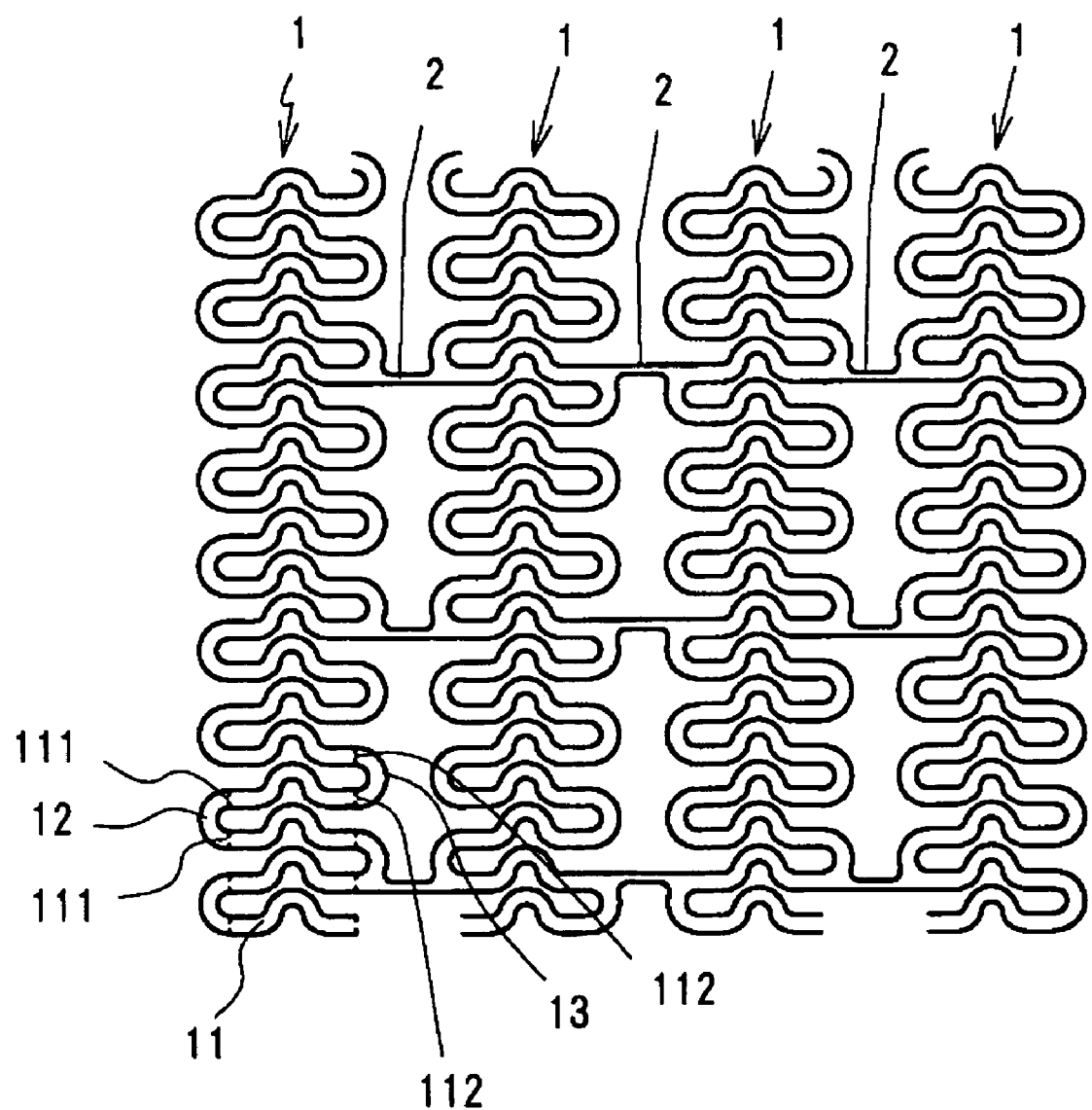
FIG. 4 is a development elevation of a stent according to another embodiment of the present invention.

FIG. 4 illustrates another embodiment of the present invention, in which a stent is a tubular member comprising a plurality of lumen size-holding portions 1 and connecting portions 2 for longitudinally connecting the lumen size-holding portions 1 with one another. The stent has the same construction as that of the stent shown in FIG. 1 except for that lumen size-holding portions 1 are connected every two curved pattern portions to one another by connecting portions 2.

Figure 5:
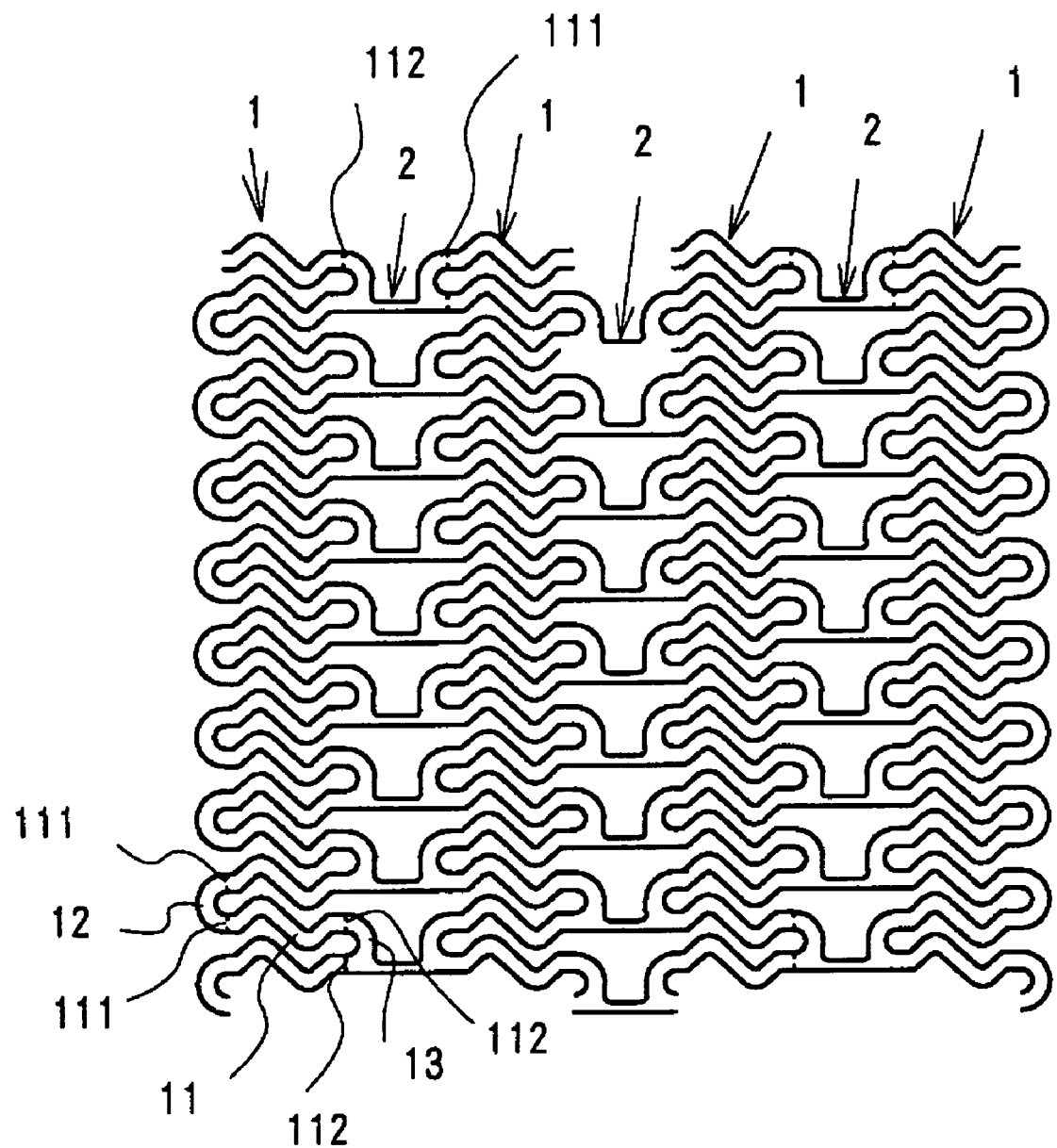
FIG. 5 is a development elevation of a stent according to another embodiment of the present invention.

FIG. 5 illustrates still another embodiment of the present invention, in which a stent comprises lumen size-holding portions 1 comprised of a first curved pattern portion 11, a second curved pattern portion 12 and a third curved pattern portion 13. The first curved pattern portion 11 is comprised of a sine waveform portion 113, and two straight portions 114, 115 extending from both ends thereof. Other portions are the same as those of the stent illustrated in FIG. 1.

(Flexibility Test)

Analysis of stress was made on stents having various development plans as illustrated in Table 1, to compare the flexibility of the stents. Results are shown in FIG. 6.

Figure 6:
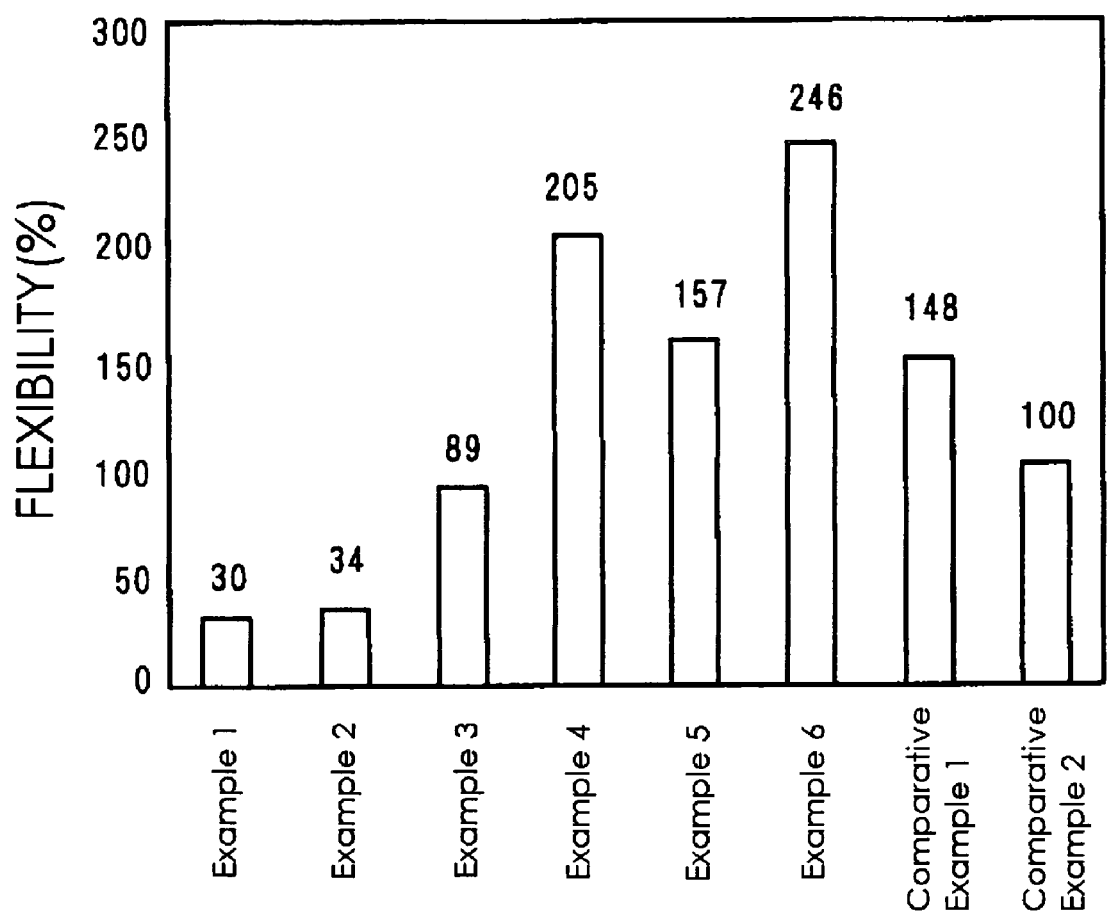
FIG. 6 is a graph illustrating comparison of the flexibility between the stent of the present invention and that of the prior art.

As will be understood from FIG. 6, the stents of the present invention possess flexibility considerably superior to those of the prior art (comparison between Example 6 and Comparative Example 2). Further, it would be seen that, if they are the same in cross section, the flexibility of the stent is improved by decreasing the sectional area (comparison between Example 4 and Example 5), or by lengthening the connecting portions 2 between the adjacent lumen size-holding portions 1 (comparison between Example 5 and Example 6), or by decreasing the number of the connecting portions 2 (comparison between Example 1 and Example 3 or 4). It would be seen that the flexibility of the stent varies with the configuration of the first curved portion (comparison between Example 1 and Example 2). It can be seen that the flexibility of the stent is improved by providing the repeated patterns with the first curved portions (comparison between Example 4 and comparative Example 1).

TABLE 1

Figure 7:
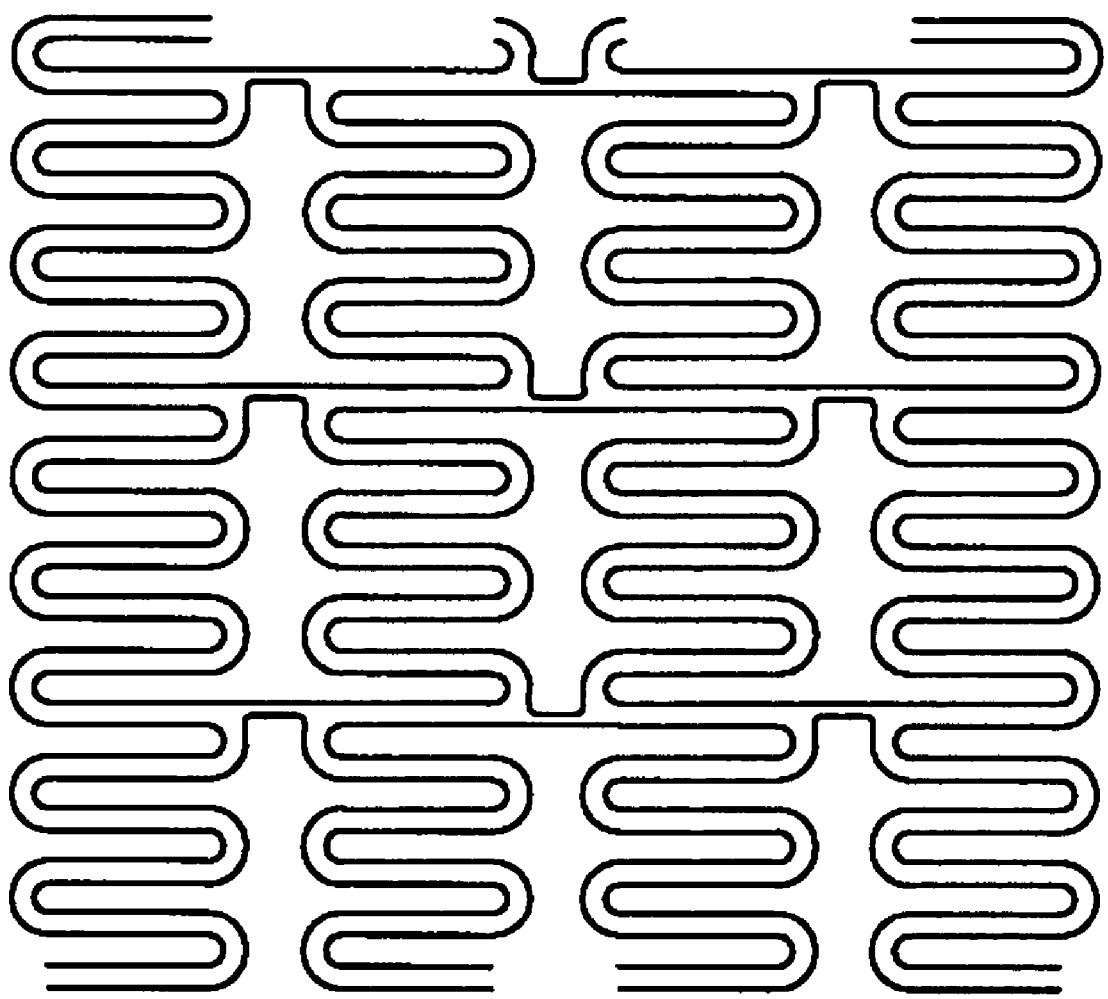
FIG. 7 is a development elevation of a stent with first curved pattern portions being removed from the stent of the present invention.
Figure 8:
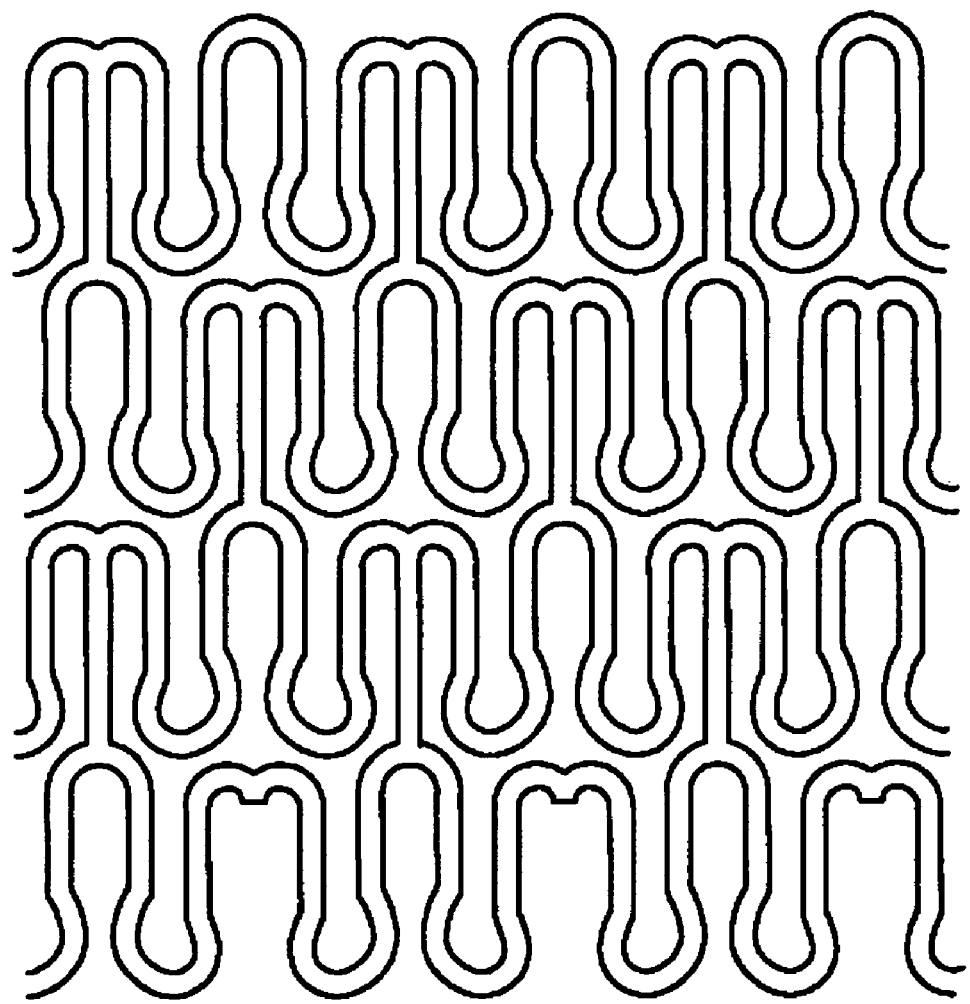
FIG. 8 is a development elevation of a stent of the prior art.

| | Remarks |
|---|---|
| Example 1 | FIG. 2 |
| Example 2 | FIG. 5 |
| Example 3 | Same with lumen size-maintaining portion of FIG. 2, connected alternately by joint portions |
| Example 4 | FIG. 4 |
| Example 5 | FIG. 4, but part shape and size of joints are the same as those of FIG. 8. |
| Example 6 | FIG. 4, length, part shape and size of joints are the same with those of FIG. 8 |
| Comparative Example 1 | FIG. 7, first curved pattern portions in FIG. 4 being omitted. |
| Comparative Example 2 | FIG. 8 (Prior art) |

The invention claimed is:

1. A stent comprised of a tubular member comprising cylindrical lumen size-holding portions for holding a lumen of a living body open, and connecting portions for longitudinally connecting said lumen size-holding portions adjacent to one another, wherein said lumen size-holding portions are configured into repeated patterns running vertically under a condition of being developed in a plane, said repeated pattern comprising:

a plurality of first curved pattern portions vertically arranged in a row and each having first and second ends and an axis extending in a lateral direction, said first curved pattern portion being composed of a semicircular or sine-wave pattern segment and two linear segments laterally extending from both ends of said semicircular or sine-wave pattern segment;

second curved pattern portions each having a semicircular shape and an axis extending in a vertical direction, said second curved pattern portion connecting the first end of said first curved pattern portion located at an even-numbered position from the bottom and the first end of the first curved pattern portion located on the downside of said even-numbered, first curved pattern portion; and third curved pattern portions each having a semicircular shape and an axis extending in the vertical direction, said third curved pattern portion connecting the second end of the first curved pattern portion located at the even numbered position and the second end of the first curved pattern portion located on the upside of said even-numbered, first curved pattern portion.

2. The stent according to claim 1, wherein the neighboring lumen-size-holding portions are connected by connecting the first end of said lumen size-holding portion to the second end of the other lumen size-holding portion with the connecting portions.

3. The stent according to claim 2, wherein the connecting portions are in a straight form.

4. The stent according to claim 2, wherein the connecting portions are formed in a curved form.

5. The stent according to claim 2, wherein the neighboring lumen-size-holding portions are mirror symmetry about connecting portions.

6. The stent according to claim 1, wherein the connecting portions are in a straight form.

7. The stent according to claim 1, wherein the connecting portions are formed in a curved form.

8. The stent according to claim 1, wherein the neighboring lumen-size-holding portions are mirror symmetry about connecting portions.

9. The stent according to claim 1, wherein the lumen size-holding portions 1 of at least both ends are connected with the connecting portions 2 every one or two repeated patterns.

10. The stent according to claim 1, wherein the stent is made of a biocompatible material or bioabsorbable material.

11. The stent according to claim 10, wherein the biocompatible material is a material selected from the group consisting of stainless steel, tungsten, tantalum, and nickel-titanium alloys.

12. The stent according to claim 11, wherein the stent is coated with a medicine for prevention of restenosis.

13. The stent according to claim 10, wherein the bioabsorbable material is a material selected from the group consisting of polylactic acid, polyglycolic acid, polyglactin, poly(dioxanone), poly(dioxanone), polyglyconate, copolymers of polyglycolic acid and $\epsilon$-caprolactam, and copolymers of lactic acid an $\epsilon$-caprolactam.

14. The stent according to claim 13, wherein the stent is coated with a medicine for prevention of restenosis.

15. The stent according to claim 10, wherein the stent is coated with a medicine for prevention of restenosis.

16. The stent according to claim 15, wherein said medicine for prevention of restenosis is a medicine selected from the group consisting of sirolimus, taxol and actinomycin-D.

17. The stent according to claim 1, wherein the stent is coated with a biocompatible material.

18. The stent according to claim 17, wherein, the biocompatible material is a material selected from the group consisting of carbon, gold, platinum, phosphorylcholine, heparin and fibrin.

19. The stent according to claim 1, wherein said first curved pattern portion is composed of a semicircular segment and two straight segments extending from both ends of said semicircular segment in a longitudinal direction of the stent.

20. The stent according to claim 1, wherein said first curved pattern portion is composed of a sine-wave pattern segment and two straight segments extending from both ends of said sine-wave pattern segment in a longitudinal direction of the stent.

* * * * *